United States Patent
Yu et al.

(10) Patent No.: US 10,369,152 B2
(45) Date of Patent: Aug. 6, 2019

(54) METHODS AND COMPOSITIONS FOR THE TREATMENT OR PREVENTION OF ABNORMAL BONE FORMATION IN A SOFT TISSUE

(71) Applicant: THE BRIGHAM AND WOMEN'S HOSPITAL, INC., Boston, MA (US)

(72) Inventors: Paul B. Yu, Boston, MA (US); Jana Bagarova, Boston, MA (US); Devaveena Dey, Boston, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 0 days.

(21) Appl. No.: 15/550,139

(22) PCT Filed: Feb. 12, 2016

(86) PCT No.: PCT/US2016/017712
§ 371 (c)(1),
(2) Date: Aug. 10, 2017

(87) PCT Pub. No.: WO2016/130897
PCT Pub. Date: Aug. 18, 2016

(65) Prior Publication Data
US 2018/0021340 A1    Jan. 25, 2018

Related U.S. Application Data

(60) Provisional application No. 62/115,758, filed on Feb. 13, 2015.

(51) Int. Cl.
*A61K 31/517*    (2006.01)
*A61K 45/06*    (2006.01)
(Continued)

(52) U.S. Cl.
CPC ........... *A61K 31/517* (2013.01); *A61K 45/06* (2013.01); *C07D 401/12* (2013.01);
(Continued)

(58) Field of Classification Search
CPC .................................................. A61K 31/517
See application file for complete search history.

(56) References Cited

U.S. PATENT DOCUMENTS

2007/0049588 A1* 3/2007 Smith ................. C07D 409/04
514/231.8
2010/0184791 A1    7/2010 Li
2011/0028488 A1    2/2011 Green

FOREIGN PATENT DOCUMENTS

WO    2001/094341 A1    12/2001
WO    2006/064217 A2    6/2006
WO    WO2015/069217    *   5/2015

OTHER PUBLICATIONS

Chen et al., "Combined Src and aromatase inhibition impairs human breast cancer growth in vivo and bypass pathways are activated in AZD0530-resistant tumors", Clinical Cancer Research 15(10)3396-3405 (2009).

(Continued)

*Primary Examiner* — San Ming R Hui
(74) *Attorney, Agent, or Firm* — Nixon Peabody LLP; David S. Resnick; Teresa A. Ptashka

(57) ABSTRACT

Provided herein are methods and compositions for the treatment and/or prevention of abnormal bone formation in a soft tissue. In certain embodiments, the methods and compositions treat and/or prevent a disease or disorder comprising abnormal bone formation in soft tissue. Exemplary diseases or disorders that can be treated with the methods and compositions described herein include, but are not limited to, heterotopic ossification diseases such as fibrodysplasia ossificans progressive, anklyosing spondylo- (Continued)

sis, traumatic heterotopic ossification, burn- or blast-injury associated heterotopic ossification, and joint replacement surgery associated heterotopic ossification.

10 Claims, 8 Drawing Sheets

(51) Int. Cl.
*C07D 405/14* (2006.01)
*C07D 401/12* (2006.01)
*C07D 487/04* (2006.01)
*C07D 491/056* (2006.01)

(52) U.S. Cl.
CPC ......... *C07D 405/14* (2013.01); *C07D 487/04* (2013.01); *C07D 491/056* (2013.01); *A61K 2300/00* (2013.01)

(56) References Cited

OTHER PUBLICATIONS

Lewis et al., "Serum regulation of Id1 expression by a BMP pathway and BMP responsive element", Biochim Biophys Acta 1829(10):1147-1159 (2013).

Theurl et al., "Pharmacologic inhibition of hepcidin expression reverses anemia of chronic inflammation in rats", Blood 118(18):4977-4981 (2011).

Hannon et al., "Effects of the Src kinase inhibitor saracatinib (AZD0530) on bone turnover in healthy men: a randomized, double-blind, placebo-controlled, multiple-ascending-dose phase I trial", J Bone Miner Res 25(3) 463-471 (2010).

Soriano et al., "Targeted disruption of the c-src proto-oncogene leads to osteopetrosis in mice", Cell 64(4) 693-702 (1991).

\* cited by examiner

CAG-Z-eGFP-ACVR1$^{Q207D}$ T vehicle    AZD-0530

METHODS AND COMPOSITIONS FOR THE TREATMENT OR PREVENTION OF ABNORMAL BONE FORMATION IN A SOFT TISSUE

CROSS-REFERENCE TO RELATED APPLICATION

This application is a 35 U.S.C. § 371 National Phase Entry Application of International Application No. PCT/US2016/017712, filed Feb. 12, 2016, which designates the U.S. and which claims benefit under 35 U.S.C. § 119(e) of U.S. Provisional Application No. 62/115,758, filed Feb. 13, 2015, the contents of each of which are herein incorporated by reference in their entireties.

FIELD OF THE DISCLOSURE

The present disclosure relates to the treatment and/or prevention of a disease or disorder comprising abnormal bone growth in a soft tissue of a subject.

BACKGROUND

Heterotopic ossification (HO) involves unwanted bone growth that may be characterized by inappropriate differentiation of cells into bone-forming cells. This condition leads to bone formation, usually near joints, where the bone formation often limits the mobility of the joint. HO may follow neurological injury and direct injury to soft tissue such as muscles or connective tissue around the joint in which HO later develops.

There are three recognized etiologies of HO: traumatic, neurogenic, and genetic. Traumatic HO typically follows fractures, dislocations, operative procedures, and severe burns. Most commonly, HO is seen around the hip after fracture and open reduction-internal fixation (ORIF) procedures or total hip arthroplasties (THA). As well, HO is often associated with pathologies such as traumatic brain injury (TBI), spinal cord injury (SCI), infections of the central nervous system (CNS), tumors, strokes, tetanus, polio, tabes dorsalis, multiple sclerosis, and selective posterior rhizotomy. The presence of idiopathic muscle spasticity is also associated with the development of HO.

SUMMARY

Provided herein are methods and compositions for the treatment and/or prevention of abnormal bone formation in a soft tissue. In certain embodiments, the methods and compositions treat and/or prevent a disease or disorder comprising abnormal bone formation in soft tissue. Exemplary diseases or disorders that can be treated with the methods and compositions described herein include, but are not limited to, heterotopic ossification diseases such as fibrodysplasia ossificans progressive, anklyosing spondylosis, traumatic heterotopic ossification, burn- or blast-injury associated heterotopic ossification, and joint replacement surgery associated heterotopic ossification.

Accordingly, provided herein in one aspect is a method for treating and/or preventing the formation of abnormal bone in a soft tissue of a subject, the method comprising: administering a therapeutically effective amount of a pharmaceutical composition comprising AZD0530 or AZD0424.

In one embodiment of this aspect and all other aspects provided herein, the subject is determined to have or be at risk of having abnormal bone formation prior to treatment.

In another embodiment of this aspect and all other aspects provided herein, the subject has been subjected to a musculoskeletal trauma, a spinal cord injury or a central nervous system injury.

In another embodiment of this aspect and all other aspects provided herein, the formation of abnormal bone is associated with a heterotopic ossification disease.

In another embodiment of this aspect and all other aspects provided herein, the heterotopic ossification disease is selected from the group consisting of: acquired heterotopic ossification, fibrodysplasia ossificans progressive, anklyosing spondylosis, traumatic heterotopic ossification, burn- or blast-injury associated heterotopic ossification, and joint replacement surgery associated heterotopic ossification.

In another embodiment of this aspect and all other aspects provided herein, the therapeutically effective amount of AZD0530 comprises a dose within the range of 5 mg/kg to 250 mg/kg.

In another embodiment of this aspect and all other aspects provided herein, the therapeutically effective amount of AZD0530 does not cause weight loss greater than 20% of total body mass.

In another embodiment of this aspect and all other aspects provided herein, the soft tissue comprises muscles, tendons, ligaments and/or fascia.

In another embodiment of this aspect and all other aspects provided herein, at least one additional agent is administered to the subject.

In another embodiment of this aspect and all other aspects provided herein, the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-1 signaling.

Also provided herein in another aspect is a composition for the treatment of abnormal bone formation in soft tissue, the composition comprising: a therapeutically effective amount of AZD0530 and a pharmaceutically acceptable carrier.

In one embodiment of this aspect and all other aspects provided herein, the therapeutically effective amount of AZD0530 is lower than the dose of AZD0530 generally used for treatment of cancer and other oncologic diseases (e.g., 175-200 mg/day).

In another embodiment of this aspect and all other aspects provided herein, the composition further comprising at least one additional agent.

In another embodiment of this aspect and all other aspects provided herein, the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-1 signaling.

In another embodiment of this aspect and all other aspects provided herein, the therapeutically effective amount of AZD0530 or AZD0424 in combination with at least one additional agent comprises a synergistic effect on reducing or preventing abnormal bone formation as compared to the effect of each agent alone.

In another embodiment of this aspect and all other aspects provided herein, the therapeutically effective amount of AZD0530 comprises a dose within the range of 5 mg/kg to 200 mg/kg.

In another embodiment of this aspect and all other aspects provided herein, the therapeutically effective amount of AZD0530 comprises a dose within the range of 100-200 mg/kg.

In another embodiment of this aspect and all other aspects provided herein, the therapeutically effective amount of AZD0530 comprises a dose within the range of 20 mg/kg to 100 mg/kg.

Another aspect provided herein relates to a method to prevent or treat anemia of inflammation, the method comprising administration of an inhibitor of the BMP type I serine-threonine kinase receptor to a subject.

In one embodiment of this aspect and all other aspects provided herein, the BMP type I serine-threonine receptor is ALK2 or ALK3.

In another embodiment of this aspect and all other aspects provided herein, the inhibitor is AZD-0530 or AZD0424.

In another embodiment of this aspect and all other aspects provided herein, the subject is a human.

DETAILED DESCRIPTION

Figure 1A:
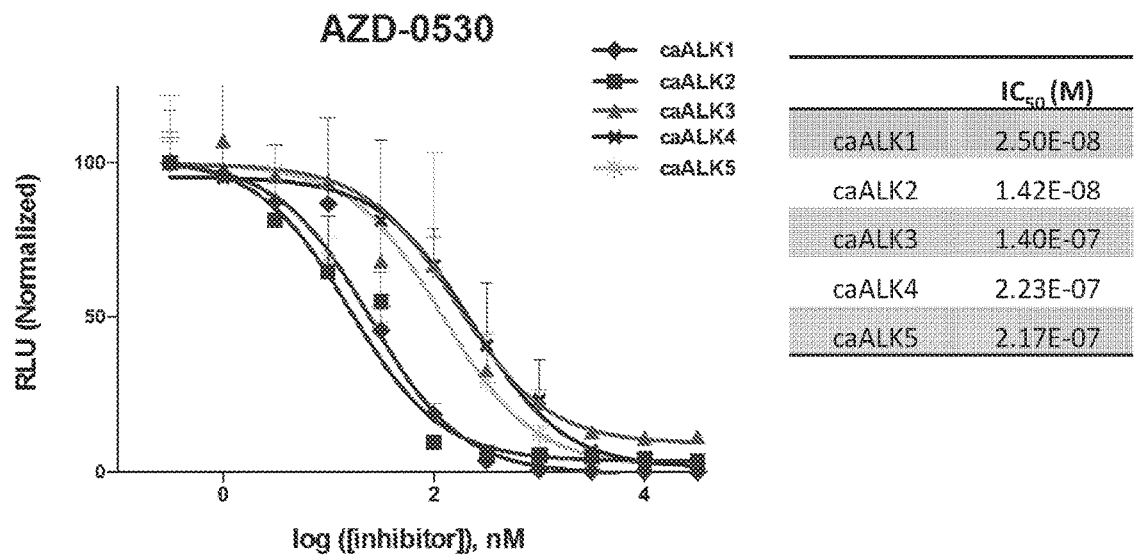
FIGS. 1A-1C. AZD-0530 is a selective inhibitor of BMP versus TGF-β type I receptor activity in cells. Inhibition curves of BMP and TGF-β transcriptional activity mediated by constitutively activated ALK1-5 in a cell-based luciferase reporter assays. Representative inhibition curves for AZD-0530 (FIG. 1A), LDN-193189 (FIG. 1B), and LDN-212854 (FIG. 1C), against constitutively active BMP (ALK1, 2 and 3) and TGF-β (ALK4 and 5) type I receptors, based on the activity of BMP responsive promoter element luciferase (BRE-Luc) and TGF-β responsive luciferase (CAGA-Luc) respectively. AZD-0530 exhibits a similar selectivity profile to LDN-193189, but with approximately 10-fold decreased potency against all receptors. Data shown are representative of more than 3 independent experiments, with data plotted as mean±S.E.M. (n=3 replicates)

The methods and compositions provided herein are based, in part, on the discovery that AZD0530 acts as a BMP inhibitor by inhibiting signaling through ALK2, a BMP type I receptor. In addition, AZD0530 is shown herein to be effective in the treatment and/or prevention of abnormal bone formation in soft tissue. Accordingly, provided herein are methods and compositions for the treatment of abnormal bone formation in soft tissue, comprising treatment with AZD0530 or AZD0424.

Definitions

"AZD0530" is also known in the art as saracatinib. The chemical name of AZD is 4-Quinazolinamine, N-(5-chloro-1,3-benzodioxol-4-yl)-7-[2-(4-methyl-1-piperazinyl)ethoxy]-5-[(tetrahydro-2H-pyran-4-yl)oxy]-Quinazolin-amine. N-(5-chloro-1,3-benzodioxol-4-yl)-7-[2-(4-methyl-1-piperazinyl)ethoxy]-5-[(tetrahydro-2H-pyran-4-yl)oxy]-N-(5-chloro-1,3-benzodioxol-4-yl)-7-[2-(4-methylpiperazin-1-yl)ethoxy]-5-[(tetrahydro-2H-pyran-4-yl)oxy]quinazolin-4-amine.

AZD0424 is structurally very similar to AZD-0530 and has very similar biochemical activity, including inhibition of BMP type I receptors As used herein, the term "soft tissue" is used to refer to tissues that connect, support or surround other structures and organs of the body. The term "soft tissue" can refer to muscles, ligaments, tendons, fascia, skin, fibrous tissues, fat, synovial membranes, nerves and/or blood vessels.

As used herein, the term "abnormal bone formation" refers to the generation or bone in an area, such as a soft tissue, where bone normally does not exist.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In another embodiment, the subject is a domesticated animal including companion animals (e.g., dogs, cats, rats, guinea pigs, hamsters etc.).

As used herein, the term "at risk of having abnormal bone formation" refers to a subject that has been exposed to conditions that are known to cause abnormal bone formation in a population of subjects. While not every subject exposed to such conditions will go on to have abnormal bone formation, but all subjects exposed to these conditions can be considered to be "at risk." Such conditions typically include a trauma, for example, a musculoskeletal trauma, a central nervous system injury or a spinal cord injury.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

Heterotopic Ossification Diseases

The term "heterotopic ossification" refers to the abnormal formation of bone in soft tissue where bone typically does not exist. Acquired heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis and burns. Examples of musculoskeletal trauma include, but are not limited to, hip, knee, shoulder, or elbow arthroplasty; fractures; joint dislocations; or soft-tissue trauma, with the *musculus* quadriceps femoris and *musculus brachialis*. Acquired heterotopic ossification can also be associated with fever, swelling, and erythema (e.g., local, patchy reddening of the skin). In one embodiment, neurogenic heterotopic ossification is not associated with local trauma.

Genetic diseases fibrodysplasia ossificans progressive (FOP) and progressive osseous heterplasia (POH) are the most severe manifestations of heterotopic bone formation. FOP occurs rarely and is a result of a mutation in ACVR1, which encodes a bone morphogenetic protein type I receptor. Patients with POH have inactivating mutations of the GNAS gene, which also can give rise to Albright's hereditary osteodystrophy (AHO) when the mutations are inherited from the mother.

Myositis ossifican circumscripta is characterized by the intramuscular proliferation of fibroblasts, new bone, and/or cartilage.

HO typically occurs between 3 weeks and 12 weeks following an injury. Heterotopic ossification can be reliably diagnosed by computed tomography, bone scintigraphy and ultrasonography. Two to six weeks later, the abnormal bone formation has progressed to the point that it is detectable by radiography. Bony maturation typically occurs within six months.

Conventional Treatment of Heterotopic Ossification:

Conventional treatment usually involves non-steroidal anti-inflammatory drugs (indomethecin, rofecoxib), or bisphosphonate (etidronate, pamidronate), Coumadin/warfarin, salicylates, and/or local radiation can also be administered. Often, surgery is the only option for treatment.

Outcome of treatment can be measured by a standard radiological grading system for HO, which includes measurements related to changes in range of motion in the affected joint measured by goniometry, mean length of time to objective improvement of HO-related clinical symptoms or signs, changes in standardized functional or joint-specific measures.

Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while other findings have suggested that in some contexts excess BMP signaling might be pathogenic (Waite et al. *Nat. Rev. Genet.* 4:763-773, 2005; Yu et. *J. Biol. Chem.* 280:24443-24450, 2003). AZD0530 (also known as saracatinib) is an inhibitor of ALK2, a BMP type 1 receptor and can be used to disrupt signaling through the BMP pathway.

A. Treatment of Anemia, Including Iron Deficiency and Anemia of Chronic Disease

For a review, see Weiss et al. *N. Engl. J. Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J. Med.* 352:1011-1023, 2005). It has been shown that stimulating hepatoma cell lines with IL-6 induces hepcidin expression, while treatment with a BMP antagonist abrogates IL-6-induced hepcidin expression (Yu et al. *Nat. Chem. Biol.* 4:33-41, 2008). Moreover, the inventors have previously found that BMP antagonists can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by the inventors' previous finding that BMP antagonists can inhibit hepcidin expression and raise serum iron levels in vivo (data not shown). Taken together these data indicate that iron- and inflammation-mediated regulation of hepcidin and circulating iron levels require BMP signaling. Thus, AZD0530, which disrupts BMP signaling through ALK2 can be used to alter iron availability in diverse circumstances for therapeutic benefit. In addition, AZD0424, which also disrupts BMP signaling through BMP type 1 receptors, can be used to alter iron availability in diverse circumstances for therapeutic benefit.

Pharmaceutical compositions as described herein can be used in anemic states to (i) augment the efficacy of dietary iron or oral iron supplementation (which is safer than intravenous administration of iron) to increase serum iron concentrations; (ii) augment build-up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

B. Treatment of Fibrodysplasia Ossificans Progressiva (FOP)

FOP is caused by the presence of a constitutively-active mutant form of ALK2 in affected individuals (Shore et al. *Nat. Genet.* 38:525-527, 2006). A specific inhibitor of BMP signaling such as AZD0530 or AZD0424 can be used to prevent excessive bone formation in response to trauma, musculoskeletal stress or inflammation. Such compounds can also be used to aid in regression of pathologic bone. AZD0530 or AZD0424 can be administered systemically or locally to concentrate or limit effects to areas of trauma or inflammation.

AZD0530, an ALK2 inhibitor, can be used as chronic therapy to suppress spontaneous bone formation in individuals who are highly susceptible. Alternatively, AZD0424 can be used as a chronic therapy to suppress spontaneous bone formation in individuals who are highly susceptible. Transient therapy can be used to prevent abnormal bone formation in FOP individuals who develop osteomas or pathologic bone most frequently in association with trauma by administration before, during, or even after the traumatic incident. Transient therapy with BMP inhibitors (e.g., AZD0530 or AZD0424) as described herein can be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituxumab, etanercept, or similar drugs) may increase the effectiveness of BMP antagonists in inhibiting heterotopic bone formation in this disorder.

A mouse model of FOP has been developed in which expression of a constitutively-active mutant form of ALK2 is induced by injecting the popliteal fossa of a genetically-modified mouse with an adenovirus directing expression of Cre recombinase. This model reproduces the ectopic calcification and disability seen in FOP patients and is used herein for efficacy testing of AZD0530 and AZD0424 (data for AZD0424 not shown).

C. Treatment of Cancers

Excessive BMP signaling, which could arise due to over-expression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J. Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Clin. Cancer Res.* 9:6046-6051, 2003; Kim et al. *Oncogene* 23:7651-7659, 2004). If increased BMP activity associated with BMP over-expression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

AZD0530 and AZD0424 are contemplated herein for use in treating cancer, for example, they can be used to slow or arrest the growth or metastasis of such tumor cells (as well as other tumor constituent cell types) for clinical benefit, either as adjunctive or primary chemotherapy. Also, BMP inhibitors as described herein can be used to interfere with the bone metastatic properties of certain types of cancers (e.g., adenocarcinoma, such as prostate and breast carcinomas). In addition, AZD0530 and AZD0424 as described herein can be used to inhibit osteoblastic activity in tumors that either form bone or are bone-derived, such as osteosarcomas (as adjunctive or primary chemotherapy). Further, AZD0530 and AZD0424 as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement.

D. Treatment of Pathologic Bone Formation

Compositions as described herein can be used to treat or ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compositions as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. *Orthop. Rev.* 21:1319-1326, 1992.). Head trauma and burn injury can also induce heterotopic bone formation markedly impairing patient rehabilitation and recovery. Treatment with AZD0530 or AZD0424 as described herein, optionally in addition to anti-inflammatory medications usually prescribed for such a condition (e.g., non-steroidal anti-inflammatory drugs such as indomethacin or ibuprofen) can help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

E. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

Pharmaceutical compositions as described herein can be used to inhibit vascular or valvular calcific disease alone or in combination with atheromatous disease, renal disease, renal osteodystrophy or parathyroid disease.

Pharmaceutical compositions as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing can be temporarily "suspended" by use of AZD0530 as described herein, until definitive surgery or manipulation can be performed. This could prevent the need for subsequent intentional re-fracture in order to ensure correct apposition of bone fragments, for example. It is expected that upon stopping administration of AZD0530 normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP antagonist as described herein via diffusion from a local implant or matrix) can be used to inhibit fracture healing or prevent fracture calluses at the critical areas.

F. Immune Modulation Via BMP Antagonists

BMPs have been reported to attenuate the inflammatory or immune response (Choi et al. Nat. Immunol. 7:1057-1065, 2006; Kersten et al. BMC Immunol. 6:9, 2005), which can impair an individual's ability to fight infections (i.e., viral, bacterial, fungal, parasitic, or tuberculosis). AZD0530, an inhibitor of BMP signaling through ALK2, can be used to augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP antagonists as described herein may also be effective in some contexts for the intentional induction of immune tolerance (i.e., in allotransplantation or autoimmunity).

G. Treatment of Skin Diseases

Expansion of Cultured Keratinocytes—

In vitro, BMPs inhibit keratinocyte proliferation and promote differentiation (reviewed in Botchkarev et al. Differentiation 72:512-526, 2004). In patients in need of skin grafting (e.g., after burns), skin grafts are made from cultured keratinocytes. The keratinocytes can be derived from other animals (xenografts), but these are only temporary as they are typically rejected by the immune system. Keratinocytes can be derived from the patient themselves and can be grown into sheets of cells in the laboratory (cultured epithelial autografts). It is unlikely that the patient will reject keratinocytes derived from his/her own body. Addition of BMP antagonists as described herein to keratinocyte cultures can be used to facilitate keratinocyte proliferation enabling patients to receive grafts sooner.

Improved Epithelialization—

BMP6 is highly expressed in skin injury, and high levels of BMP6 are detected in chronic human wounds of different etiologies (Kaiser et al. J. Invest. Dermatol. 111:1145-1152, 1998). In mice overexpressing BMP6 in their skin, reepithelialization and healing skin wounds were significantly delayed (Kaiser et al. J. Invest. Dermatol. 111:1145-1152, 1998). Improved epithelialization can reduce scar formation. Topical or systemic administration of AZD0530 is contemplated herein to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of Hair Growth—

Growth of hair follicles on the scalp is cyclic with three phases: anagen (the growth phase), catagen (the involutional phase), and telogen (resting phase). Recent evidence indicates that BMP signals delay the transition from telogen to anagen (Plikus et al. Nature 451:340-344, 2008). Inhibition of BMP signaling using AZD0530 or AZD0424 as described herein can shorten the telogen phase and increase the number of follicles in the anagen phase. AZD0530 or AZD0424 can be used to treat circumstances wherein hair follicles are insufficient or when hairs are being lost more frequently than they are grown. These circumstances include androgenetic alopecia (male pattern balding), alopecia greata, and telogen effluvium.

Treatment of Psoriasis—

Psoriasis is an inflammatory skin disorder which can occur following skin trauma and the ensuing repair and inflammation (Koebner phenomenon). BMPs can participate in repair and inflammatory mechanisms that cause psoriasis, since over-expression of BMP6 in the skin of mice leads to skin lesions similar to those seen in patients with psoriasis (Blessing et al. J. Cell. Biol. 135:227-239, 1996). AZD0530 or AZD0424 can be administered topically or systemically to treat established psoriasis or prevent its development after skin injury.

Treatment of Corneal Scarring—

BMP6 expression is associated with conjunctival scarring (Andreev et al. Exp. Eye Res. 83:1162-1170, 2006). AZD0530 or AZD0424 can be used to prevent or treat corneal scarring and the resulting blindness.

H. Treatment of Systemic Hypertension

Infusion of BMP4 induces systemic hypertension in mice (Miriyala et al. Circulation 113:2818-2825, 2006). Vascular smooth muscle cells express a variety of BMP ligands. BMPs increase the expression of voltage gated potassium channels and thereby increase constriction of vascular smooth muscle (Fantozzi et al. Am. J. Physiol. Lung Cell. Mol. Physiol. 291:L993-1004, 2006). Thus, AZD0530 or AZD0424 is contemplated herein to inhibit BMP signaling, which can be used to reduce blood pressure. Sustained reduction of blood pressure in patients with hypertension is expected to prevent myocardial infarction, congestive heart failure, cerebrovascular accidents, and renal failure. Treatment as described herein can be used to target the hypertension in specific vascular beds, such as in pulmonary hypertension via local delivery (e.g., via aerosol).

I. Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. Circ. Res. 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. J. Biol. Chem. 280:24443-24450, 2008) reported that BMPRII deficiency paradoxically increases BMP signaling by subsets of BMP ligands, and thus increased BMP signaling may actually contribute to the development of pulmonary hypertension.

Pharmaceutical compositions comprising AZD0530 or AZD0424 can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated as described herein are expected to have a decrease in shortness of breath, right ventricular hypertrophy, and right ventricular failure.

J. Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. Am. J. Physiol. Heart. Circ. Physiol. 293:H3396-3403, 2007). Inhibition of BMP-10 signaling can be used to prevent/treat ventricular hypertrophy. Ventricular hypertrophy can lead to congestive heart failure due to diastolic dysfunction. Pharmaceutical compositions comprising AZD0530 or AZD0424 may prevent/treat congestive heart failure.

K. Treatment of Neurologic Disorders

Treatment of Spinal Cord Injury and Neuropathy—

BMPs are potent inhibitors of axonal regeneration in the adult spinal cord after spinal cord injury (Matsuura et al. J. Neurochem. 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. J. Cell. Biol. 173:47-58, 2006; Kyoto et al. Brain Res. 1186:74-86, 2007). RGMa enhances BMP signaling (Babitt et al. J. Biol. Chem. 280:29820-29827, 2005) suggesting that BMP signaling may be responsible for preventing axonal growth and recovery.

Based on these considerations, treatment with AZD0530 or AZD0424 as described herein would be expected to increase axonal growth and recovery after spinal cord injury. Treatment as described herein would be expected to prevent/treat neuropathies associated with a wide spectrum of disorders including diabetes mellitus. In addition, treatment with AZD0530 or AZD0424 as described herein can be used treat both the pain and motor dysfunction associated with neuropathies.

Treatment of Neurologic Disorders Associated with Central Nervous System Inflammation—

BMP4 and 5 have been detected in multiple sclerosis and Creutzfeldt-Jakob disease lesions (Deininger et al. Acta Neuropathol. 90:76-79, 1995). BMPs have also been detected in mice with experimental autoimmune encephalomyelitis, an animal model of multiple sclerosis (Ara et al. J. Neurosci. Res. 86:125-135, 2008). Treatment as described herein can be used to prevent or treat multiple sclerosis as well as other neurologic disorders associated with central nervous system inflammation, or maladaptive injury repair processes mediated by BMP signals.

Treatment of Dementias—

Inhibitors of BMP signaling can promote neurogenesis in mouse neural precursor cells (Koike et al. J. Biol. Chem. 282: 15843-15850, 2007). Treatment with AZD0530 as described herein can be used to augment neurogenesis in a variety of neurologic disorders associated with accelerated loss of neurons including cerebrovascular accidents and Alzheimer's Disease, as well as other dementias.

Altering Memory and Learning—

BMP signaling has an important role in the development and maintenance of neurons involved in memory and cognitive behavior. For example, mice deficient in the BMP antagonist, chordin, have enhanced spatial learning but less exploratory activity in a novel environment (Sun et al. J. Neurosci. 27:7740-7750, 2007). Treatment with AZD0530 or AZD0424 as described herein can be used to alter or prevent memory or learning, for example, inducing amnesia for anesthesia or in other situations likely to cause distress, or to prevent Post-Traumatic Stress Disorder.

L. Treatment of Atherosclerosis

Abundant evidence indicates that BMP ligands are pro-inflammatory and pro-atherogenic in the blood vessel wall (Chang et al. Circulation 116:1258-1266, 2007). Knocking-down expression of BMP4 decreased inflammatory signals, whereas knocking-down BMP antagonists (eg follistatin or noggin) increased inflammatory signals. Treatment with AZD0530 or AZD0424 as described herein can be used to reduce vascular inflammation associated with atherosclerosis, autoimmune disease, and other vasculitides. By decreasing atherosclerosis, treatment as described herein would decrease acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal structure and the requirement for vascular surgery.

As BMPs and many of the BMP-induced gene products that affect matrix remodeling are overexpressed in early atherosclerotic lesions, BMP signals can promote plaque formation and progression (Bostrom et al. J Clin Invest. 91: 1800-1809. 1993; Dhore et al. Arterioscler Thromb Vasc Biol. 21: 1998-2003. 2001). BMP signaling activity in the atheromatous plaque can thus represent a form of maladaptive injury-repair, or can contribute to inflammation. Over time, BMP signals can also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, treatment as described herein can be used to limit the progression of atheromatous plaques and vascular calcification in vivo.

M. Propagation, Engraftment and Differentiation of Progenitor Cells Including Embryonic and Adult Stem Cells In Vitro and In Vivo BMP signals are important for regulating the differentiation and regeneration of precursor and stem cell populations, in some contexts and tissues preventing (while in other contexts directing) differentiation towards a lineage. Treatment with AZD0530 or AZD0424 as described herein can be used to (i) maintain a pluripotential state in stem cell or multipotent cell populations in vivo or in vitro; (ii) expand stem cell or multipotent cell populations in vivo or in vitro;

(iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the dedifferentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PIGF, and others), Sonic Hedgehog (SHH), notch, and Wnt signaling pathways to effect these changes (Okita et al. Curr. Stem Cell Res. Ther. 1:103-111, 2006). Treatment with AZD0530 or AZD0424 as described herein can be used to direct the differentiation of stem cells (e.g., embryonic stem cells) or tissue progenitor cells towards specific lineages for therapeutic application (Park et al. Development 131:2749-2762, 2004; Pashmforoush et al. Cell 117:373-386, 2004). Alternatively for certain cell populations, BMP inhibitors as described herein may be effective in preventing differentiation and promoting expansion, in order to produce sufficient numbers of cells to be effective for a clinical application. The exact dose and/or combination of AZD0530 or AZD0424 and other BMP antagonists or growth factor(s) or signaling molecule(s) may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. Curr. Stein Cell Res. Ther. 1:103-111, 2006). Use of AZD0530 or AZD0424 as described herein may be used to maintain pluripotency in the absence of LIF. Other ES cell lines require coculture with a specific feeder cell layer in order to maintain pluripotency. Use of AZD0530 or AZD0424 as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. Nat. Biotechnol. 23:607-611, 2005). Use of a pharmacologic BMP antagonist, such as AZD0530 or AZD0424, as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein antagonist of BMP such as noggin would be prohibitively expensive and entail complicated dosing. Delivery of a BMP antagonist as described herein, systemically or locally, could bias the differentiation of such precursor cells into functioning cardiomyocytes in situ.

N. Applications of Compounds in Species Other than Human

Pharmaceutical compositions as described herein can be used to treat subjects (e.g., humans, domestic pets, livestock, or other animals) by use of dosages and administration regimens that are determined to be appropriate by those of skill in the art, and these parameters can vary depending on, for example, the type and extent of the disorder treated, the overall health status of the subject, the therapeutic index of the compound, and the route of administration. Standard clinical trials can be used to optimize the dose and dosing frequency for any particular pharmaceutical composition as described herein. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used with the methods and compositions described herein are well known in the art and can be found, for example, in Remington: The Science and Practice of Pharmacy (20th edition, Ed., A. R. Gennaro), Lippincott Williams & Wilkins, 2000.

O. Inhibition of BMP Signaling in Insects

AZD0530 or AZD0424 may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and *drosophila* when this pathway is inhibited. BMP antagonists having very strong selectivity for arthropod BMP receptors versus those of humans can be used as insecticides or pest control agents that are demonstrably less toxic or more environmentally sound than current strategies.

P. Ex Vivo applications

In addition to being administered to patients in therapeutic methods, AZD0530 or AZD0424 as described herein can also be used to treat cells and tissues, as well as structural materials to be implanted into patients (see above), ex vivo. For example, the compounds can be used to treat explanted tissues that may be used, for example, in transplantation.

Pharmaceutical Compositions

AZD0530 (also known as saracatinib) or a derivative thereof or AZD0424 can be used in a pharmaceutical composition, e.g., combined with a pharmaceutically acceptable carrier, for administration to a patient. Such a composition can also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents can be included in the pharmaceutical composition to produce a synergistic effect with compounds of the invention, or to minimize side effects caused by the compound of the invention.

The pharmaceutical compositions as described herein can be in the form of a liposome or micelles in which AZD0530 or a derivative thereof or AZD0424 are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art and is therefore not described in detail herein.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use as described herein, comprises administering to a mammal in need of such treatment or use a pharmaceutically or therapeutically effective amount of AZD0530, AZD0424 or a derivative, a pharmaceutically acceptable salt or ester form thereof. Compounds as described herein can be administered in accordance with the methods described herein either alone or in combination with other therapies.

Administration of the pharmaceutical compositions or to practice the methods described herein can be carried out in a variety of conventional ways, such as oral ingestion, inhalation, or cutaneous, subcutaneous, or intravenous, intramuscular, and intraperitoneal injection.

When a therapeutically effective amount of a compound(s) or pharmaceutical composition is administered orally, such compounds or compositions can be in the form of a tablet, capsule, powder, solution or elixir. When administered in tablet form, the pharmaceutical composition can additionally contain a solid carrier such as a gelatin or an adjuvant. The tablet, capsule, and powder can contain from about 5 to 95% AZD0530 or AZD0424, and preferably from about 10% to 90% AZD0530 or AZD0424. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils can be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of the active compound (i.e., AZD0530 or AZD0424), and preferably from about 1 to 50% of the active compound.

When a therapeutically effective amount of AZD0530, AZD0424 or a composition thereof is administered by intravenous, cutaneous or subcutaneous injection, the composition can be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active compound (i.e., AZD0530 or AZD0424), an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) can also contain stabilizers, preservatives, buffers, antioxidants, or other additives known to those of skill in the art.

The amount of active compound(s) in the pharmaceutical composition will depend upon the nature and severity of the condition being treated, and on the nature of prior treatments the patient has undergone. Ultimately, the practitioner will decide the amount of compound with which to treat each individual patient. Initially, the practitioner may administer low doses of compound to observe the patient's response. Larger doses of compounds can be administered until the optimal therapeutic effect is obtained for the patient, and at that point the dosage is not increased further. It is contemplated that the various pharmaceutical compositions used to practice the methods described herein will contain about 0.1 µg to about 100 mg (preferably about 0.1 mg to about 50 mg, more preferably about 1 mg to about 2 mg) of AZD0530 or AZD0424 or additional bioactive compound per kg body weight.

The duration of intravenous therapy using the pharmaceutical composition(s) will vary, depending on the severity of the disease being treated and the condition and potential idiosyncratic response of each individual patient. It is contemplated that the duration of each administration will be in the range of 12 to 24 hours of continuous intravenous administration. Ultimately the practitioner will decide on the appropriate duration of intravenous therapy using the pharmaceutical compositions as described herein.

Combination Therapies

In certain instances AZD0530, AZD0424 or derivatives thereof as described herein can be used in combination with other current or future drug therapies, because the effects of inhibiting BMP alone may be less optimal by itself, and/or can be synergistic or more highly effective in combination with therapies acting on distinct pathways which interact functionally with BMP signaling, or on the BMP pathway itself. Some examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

Combined use of Notch modulators (e.g., gamma-secretase inhibitors) and BMP antagonists as described herein may be more effective than either agent alone in applications designed to inhibit bone differentiation, because increasing evidence suggests both pathways function cooperatively to effect cell differentiation (Kluppel et al. *Bioessays* 27:115-118, 2005).

Combined use of an Indian Hedgehog (IHH) antagonist and a BMP antagonist (e.g., AZ0530 or AZD0424) as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. *J. Biol. Chem.* 279: 18544-18549, 2004; Minina et al. *Development* 128:4523-4534, 2001). Coadministration of an IHH antagonist with AZD0530 or AZD0424 as described herein, therefore, may be more effective in inhibiting pathological bone growth due to hyperactive BMP signaling (such as in FOP), or in any of the inflammatory or traumatic disorders of pathologic bone formation described above.

In some embodiments, AZD0530 or AZD0424 is administered in combination with an agent selected from the group consisting of: a corticosteroid, a non-steroidal anti-inflammatory drug (NSAID), a lipoxygenase inhibitor, a leukotriene inhibitor, a mast cell stabilizing agent, an anti-histamine, a tumor necrosis factor (TNF) inhibitor, an IL-23 blocker, an IL1-RA therapy, a cytotoxic therapy, a bisphosphonate, an anti-rheumatic drug, CTA4-Ig therapy, anti-growth factor therapies, and an inhibitor of interleukin-1 signaling.

Exemplary corticosteroids for use in combination with AZD0530 or AZD0424 include, but are not limited to, prednisone, cortisol, and hydrocortisone. In one embodiment, the corticosteroid is prednisone.

Exemplary NSAIDs for use in combination with AZD0530 or AZD0424 include, but are not limited to, naproxen, ibuprofen, meloxicam, diclofenac, aspirin, piroxicam, sulindac, meclofenamic acid, and indomethacin.

In some embodiments, AZD0530 or AZD0424 is administered in combination with a lipoxygenase inhibitor such as meclofenamate sodium or zileuton.

Exemplary leukotriene inhibitors for use in combination with AZD0530 or AZD0424 include e.g., montelukast, zafirlukast, and pranlukast.

Non-limiting examples of mast cell stabilizing agents for use in combination with AZD0530 include, but are not limited to, cromolyn sodium, cromoglicic acid, ketotifen, olopatadine, omalizumab, pemirolast, quercetin, theophylline, caffeine, paraxanthine, aminophylline, and theobromine.

In some embodiments, AZD0530 or AZD0424 is administered in combination with an anti-histamine, for example, diphenhydramine, cetirizine, ranitidine, famotidine, chlorphenamine, chlorodiphenhydramine, and fexofenidine, among others.

Exemplary anti-tumor necrosis factor (anti-TNF) drugs contemplated for use with AZD0530 or AZD0424 include, but are not limited to, infliximab, etanercept, adalimumab, certolizumab, bupropion, and golimumab.

Exemplary inhibitors of interleukin-23 (IL-23) signaling contemplated for use with AZD0530 or AZD0424 include, but are not limited to, ustekinumab and BI-855066.

Exemplary inhibitors of interleukin-1 (IL-1) signaling or IL-1RA therapies contemplated for use with AZD0530 or AZD0424 include, but are not limited to, anakinra, canakinumab, and rilonacept.

Exemplary cytotoxic therapies for use in combination with AZD0530 or AZD0424 include, but are not limited to, methotrexate, cyclophosphamide, 5-fluorouracil, doxorubicin, vincristine, bleomycin, procarbazine, prednisolone, dacarbazine, etoposide, cisplatin, oxaliplatin, among others.

Exemplary bisphosphonates for use in combination with AZD0530 or AZD0424 include, but are not limited to, alendronate (FOSAMAX™), ibandronate (BONIVA™), risedronate (ACTONEL™, ATELVIA™), and zoledronic acid (RECLAST™).

Exemplary anti-growth factor therapies for use in combination with AZD0530 or AZD0424 include, but are not limited to, anti-PDGF, anti-FGF, and anti-VEGF therapies.

Exemplary disease modifying anti-rheumatic drugs for use in combination with AZD0530 or AZD0424 include, but are not limited to, azathioprine (IMURAN™), cyclophosphamide (CYTOXAN™), cyclosporine (NEORAL™), hydroxychloroquine (PLAQUENIL™), leflunomide (ARAVA™), methotrexate (RHEUMATREX™, TREXALL™), sulfasalazine (AZULFIDINE™), and tofacitinib (XELJANZ™), among others.

In further embodiments, AZD0530 or AZD0435 can be administered in combination with cyclosporine, mycophenylate mofetil, among others.

When used in combination, AZD0530 or AZD0424 can be administered separately or in different formulations from at least one additional agent as described herein or can be administered in a single formulation comprising AZD0530 or AZD0424 and the additional agent. AZD0530 or AZD0424 can be administered simultaneously or concurrently with the at least one additional agent. Administration of AZD0530 or AZD0424 can be administered using the same or different modes of administration (e.g., oral, intravenous, injection, etc). Administration of AZD0530 or AZD0424 and the at least one additional agent can occur simultaneously, within 15 min, within 30 min, or can be separated by at least one hour (e.g., at least 2, at least 3, at least 4, at least 5, at least 6, at least 7, at least 8, at least 9, at least 10, at least 11, at least 12 or more hours). One of skill in the art can easily determine an appropriate dosing regimen for a combination treatment comprising AZD0530 or AZD0424 and at least one additional agent, for example, to reduce side effects, to prevent metabolic interference from one of the agents, to enhance activity of AZD0530 or AZD0424, or to otherwise improve pharmacodynamic or pharmacokinetic factors.

It is contemplated herein that a combination of at least one additional agent as described above with AZD0530 or AZD0424 can produce a synergistic effect that is greater than the sum of the effects of each agent administered alone. In such embodiments, it is contemplated that a lower dose of AZD0530 or AZD0424 is administered in combination with a second agent than is required for a therapeutic effect when AZD0530 or AZD0424 is administered alone.

Dosage and Administration

The term "treatment" includes prophylaxis and therapy. Prophylaxis or treatment can be accomplished by a single administration at a single time point or multiple time points.

In one aspect, the methods described herein provide a method for treating a disease or disorder comprising abnormal bone formation in a subject (e.g., a heterotopic ossification diseases). In one embodiment, the subject can be a mammal. In another embodiment, the mammal can be a human, although the approach is effective with respect to all mammals. The method comprises administering to the subject an effective amount of a pharmaceutical composition comprising AZD0530 or AZD0424.

The dosage range for the agent depends upon the potency, and includes amounts large enough to produce the desired effect, e.g., reduction in at least one symptom of abnormal bone formation. The dosage should not be so large as to cause unacceptable adverse side effects. Generally, the dosage will vary with the type of inhibitor (e.g., an antibody or fragment, small molecule, siRNA, etc.) and with the age, condition, and sex of the patient. The dosage can be determined by one of skill in the art and can also be adjusted by the individual physician in the event of any complication. Typically, the dosage ranges from 0.1 mg/kg body weight to 1 g/kg body weight. In some embodiments, the dosage range is from 0.1 mg/kg body weight to 1 g/kg body weight, from 0.1 mg/kg body weight to 500 mg/kg body weight, from 0.1 mg/kg body weight to 250 mg/kg body weight, from 0.1 mg/kg body weight to 100 mg/kg body weight, from 0.1 mg/kg body weight to 50 mg/kg body weight, from 0.1 mg/kg body weight to 10 mg/kg body weight, from 10 mg/kg to 100 mg/kg, from 15 mg/kg to 100 mg/kg, from 20 mg/kg to 100 mg/kg, from 25 mg/kg to 100 mg/kg, from 30 mg/kg to 100 mg/kg, from 40 mg/kg to 100 mg/kg, from 50 mg/kg to 100 mg/kg, from 60 mg/kg to 100 mg/kg, from 70 mg/kg to 100 mg/kg, from 75 mg/kg to 100 mg/kg, from 25 mg/kg to 50 mg/kg, from 50 mg/kg to 200 mg/kg, from 75 mg/kg to 250 mg/kg, from 100 mg/kg to 300 mg/kg, from 100 mg/kg to 200 mg/kg, from 100 mg/kg to 400 mg/kg, from 100 mg/kg to 500 mg/kg, from 100 mg/kg to 750 mg/kg from 200 mg/kg to 1000 mg/kg, from 300 mg/kg to 1000 mg/kg, from 400 mg/kg to 1000 mg/kg, from 500 mg/kg to 1000 mg/kg, from 600 mg/kg to 1000 mg/kg, from 700 mg/kg to 1000 mg/kg, from 800 mg/kg to 1000 mg/kg, from 900 mg/kg to 1000 mg/kg, from 250 mg/kg to 750 mg/kg, from 300 mg/kg to 600 mg/kg, or any range therebetween.

In certain embodiments, the dose of the agent is at least 10 mg/kg/day; in other embodiments the dose of the agent is at least 20 mg/kg/day, at least 25 mg/kg/day, at least 30 mg/kg/day, at least 40 mg/kg/day, at least 50 mg/kg/day, at least 60 mg/kg/day, at least 70 mg/kg/day, at least 80 mg/kg/day, at least 90 mg/kg/day, at least 100 mg/kg/day, at least 125 mg/kg/day, at least 150 mg/kg/day, at least 175 mg/kg/day, at least 200 mg/kg/day, at least 250 mg/kg/day, at least 300 mg/kg/day, at least 400 mg/kg/day, at least 500 mg/kg/day or more.

In some embodiments, the dosage range of the agent for use in a human subject is from 10 mg/day to 250 mg/day, from at 15 mg/day to 200 mg/day, from 20 mg/day to 200 mg/day, from 25 mg/day to 200 mg/day, from 25 mg/day to 175 mg/day, from 25 mg/day to 150 mg/day, from 25 mg/day to 125 mg/day, from 25 mg/day to 100 mg/day, from 25 mg/day to 75 mg/day, from 25 mg/day to 50 mg/day, from 50 mg/day to 200 mg/day, from 75 mg/day to 200 mg/day, from 100 mg/day to 200 mg/day, from 125 mg/day to 200 mg/day, from 150 mg/day to 200 mg/day, from 175 mg/day to 200 mg/day, from 50 mg/day to 200 mg/day, from 50 mg/day to 175 mg/day, from 50 mg/day to 150 mg/day, from 50 mg/day to 100 mg/day, from 50 mg/day to 75 mg/day, from 75 mg/day to 200 mg/day, from 75 mg/day to 175 mg/day, from 75 mg/day to 150 mg/day, from 75 mg/day to 125 mg/day, from 75 mg/day to 100 mg/day, from 100 mg/day to 200 mg/day, from 100 mg/day to 175 mg/day, from 100 mg/day to 125 mg/day, from 125 mg/day to 200 mg/day, from 125 mg/day to 175 mg/day, from 125 mg/day to 150 mg/day, from 150 mg/day to 200 mg/day, from 150 mg/day to 175 mg/day, from 175 mg/day to 200 mg/day, or any range therebetween.

In one embodiment, the dose of AZD0530 or AZD0424 used in humans for the treatment of abnormal bone formation in soft tissue is less than the dose of AZD0530 or AZD0424 typically used in treatment of oncologic diseases and cancers.

Administration of the doses recited above can be repeated for a limited period of time. In some embodiments, the doses are given once a day, or multiple times a day, for example but not limited to three times a day. In another embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of a cancer (see "Efficacy Measurement" below). Such effective amounts can be gauged in clinical trials as well as animal studies for a given agent.

Agents useful in the methods and compositions described herein can be administered systemically or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art.

In some embodiments, the pharmaceutically acceptable formulation used to administer the active compound provides sustained delivery, such as "slow release" of the active compound to a subject. For example, the formulation can deliver the agent or composition for at least one, two, three, or four weeks after the pharmaceutically acceptable formulation is administered to the subject. Preferably, a subject to be treated in accordance with the methods described herein is treated with the active composition for at least 30 days (either by repeated administration or by use of a sustained delivery system, or both).

As used herein, the term "sustained delivery" is intended to include continual delivery of the composition in vivo over a period of time following administration, preferably at least several days, a week, several weeks, one month or longer. Sustained delivery of the active compound can be demonstrated by, for example, the continued therapeutic effect of the composition over time (such as sustained delivery of the agents can be demonstrated by continued improvement or maintained improvement in cancer symptoms in a subject).

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., tumor site). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood or skeletal muscle tissue in the ranges specified for in vivo therapies are contemplated.

Efficacy Measurement

The efficacy of a given treatment for a disorder comprising abnormal bone growth as described herein can be determined by the skilled clinician. However, a treatment is considered "effective treatment," as the term is used herein, if any one or all of the signs or symptoms of the disease or disorder is/are altered in a beneficial manner (e.g., reduced ossification, regression of abnormal bone growths, reduced pain, increased range of motion etc.), other clinically accepted symptoms or markers of disease are improved, or even ameliorated, e.g., by at least 10% following treatment with an agent comprising AZD0530 or AZD0424. Efficacy can also be measured by failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of abnormal bone growth; or (2) relieving the disease, e.g., causing regression of symptoms; and (3) preventing or reducing the likelihood of the development of a disease (e.g., ossification following trauma).

An effective amount for the treatment of a disease means that amount which, when administered to a mammal in need thereof, is sufficient to result in effective treatment as that term is defined herein, for that disease. Efficacy of an agent can be determined by assessing physical indicators of abnormal bone growth, such as e.g., reduced size of abnormal bone growth, slowed deposition of abnormal bone, regression of bone growth, improvement in mobility etc.

Examples

Results

A variety of existing multi-kinase inhibitors, typically in pre-clinical or clinical development for the treatment of oncologic disease, have been previously characterized for their kinome-wide activities using various high-throughput methodologies for assessment of kinase inhibition (Karaman M W et al., Nat Biotechnology 2008). Several known multi-kinase inhibitors that were previously described to have activity against the BMP type I receptor kinase ALK2, encoded by ACVR1, were analyzed. A number of kinases were known to have low nanomolar activity against ALK2/ACVR1, including ZD-6474 (a.k.a., Vandetinib, Kd~150 nM binding by KinomeScan), BMS-354825, (a.k.a., Dasatinib, Kd~660 nM KinomeScan), and AZD-0530 (a.k.a., Saracatinib, IC50~15-30 nM inhibition by in vitro kinase assay) (Karaman M W, Ibid., and Weisberg E, Leukemia 2012). In addition to biochemical data suggesting high affinity for or inhibition of ALK2/ACVR1, several of these compounds were shown to inhibit the signaling of BMP type I receptors including ALK2 in cells, with low nanomolar potency similar to what has been observed by in vitro kinase assays (Lewis T C and Prywes R, Biochemica et Biophysica Acta, 2013).

Figure 1B:
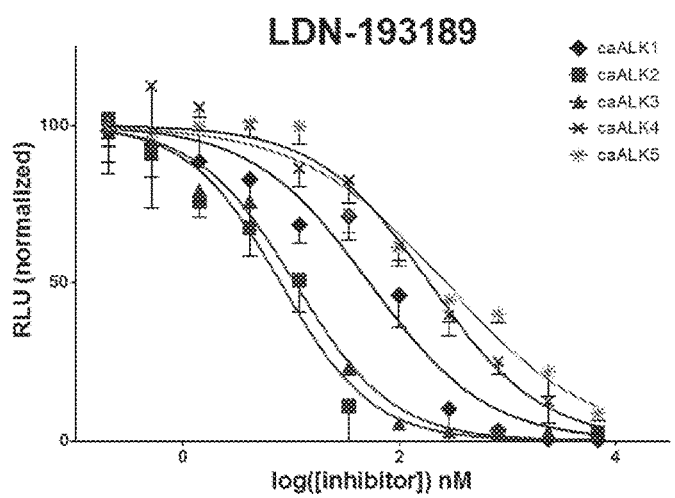
Figure 1C:
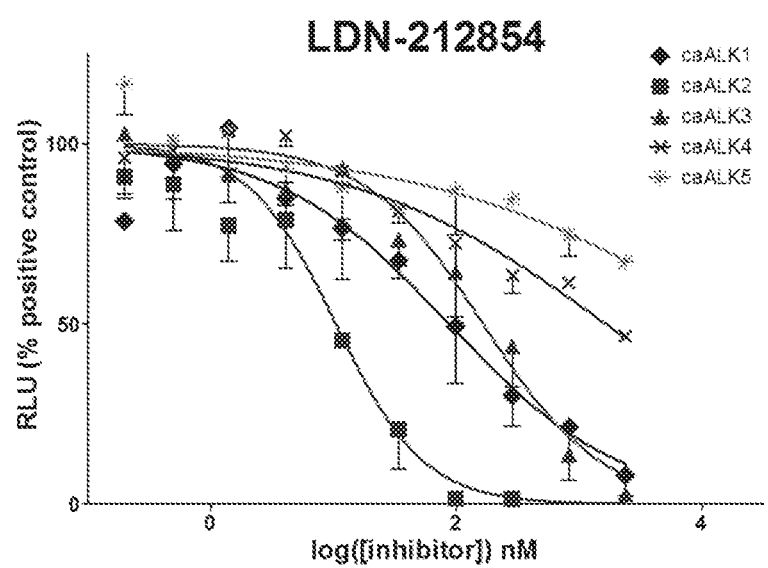
Figure 2A:
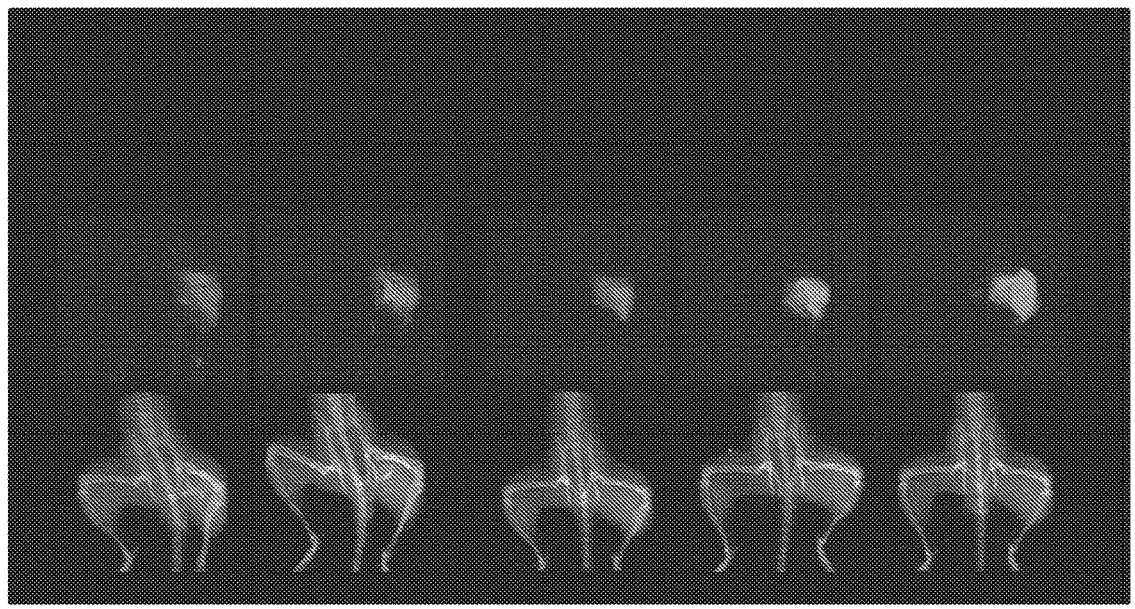
FIGS. 2A-2C. In vivo efficacy and tolerability of AZD-0530 in a mouse model of fibrodysplasia ossificans progressiva (FOP). Mice expressing an inducible constitutively-active ACVR1$^{Q207D}$ (CAG-Z-EGFP-caALK2) transgene were treated with vehicle versus AZD-0530 (25 mg/kg oral gavage daily) following administration of Ad.Cre (1.8×10$^8$ pfu intramuscularly to the left hindlimb) at P7. Recombination of the transgene was confirmed by epifluorescence imaging of the GFP reporter (FIG. 2A, top panel), while heterotopic ossification following injection of Ad.Cre was observed by X-ray (FIG. 2A, bottom panel). Heterotopic ossification following Ad.Cre injection was observed 100% of vehicle-treated mice (n=5), whereas ossification was essentially absent in all mice treated with AZD-0530 (n=4). Passive range-of-motion was progressively impaired in vehicle-treated mice starting on day 6 after Ad.Cre injection, whereas mobility was nearly completely preserved in mice treated with AZD-0530 (FIG. 2C). Importantly, this regimen was tolerated well by neonatal mice with no evidence of distress or weight-loss in the drug-treated mice relative to vehicle-treated controls (FIG. 2B).
Figure 2B:
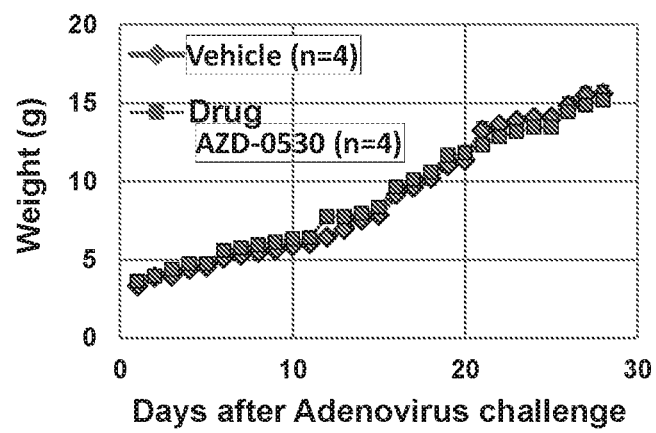
Figure 2C:
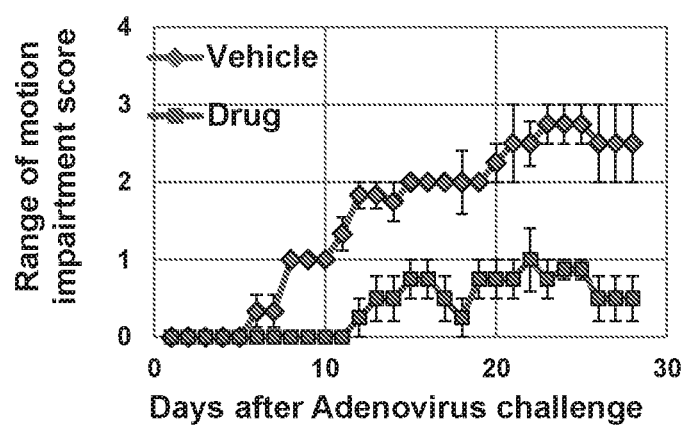
Figure 2C:
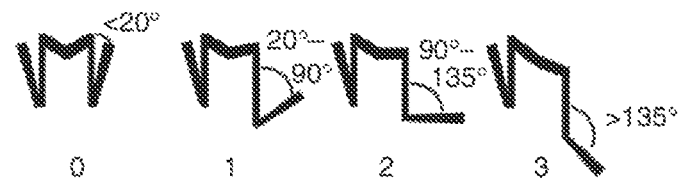

Inhibition of BMP-mediated gene transcription was measured via the activity of a BMP-response element luciferase reporter (BRE-Luc) stably expressed in the C2C12 cell line as a measure of BMP signaling inhibition, with gene expression being driven by constitutively active (ca-) forms of BMP type I receptors ALK1, ALK2, and ALK3 (FIG. 1). This was measured in comparison to the inhibition of TGF-$\beta$ or Activin signaling via CAGA-Luc reporter construct stably expressed in HEK293 cells, with gene expression being driven by constitutively active (ca-) forms of Activin/TGF=$\beta$ type I receptors ALK4 or ALK5 (FIG. 1). In these studies, compound AZD-0530, a compound originally identified as an inhibitor of Src family kinases, and investigated for is activity against Src kinases in a variety of clinical contexts, was shown to inhibit the activity of BMP type I receptor ALK2/ACVR1 with an IC50 of approximately 1.4×10$^{-8}$ M (FIG. 1), while being relatively less potent for Activin and TGF-$\beta$ receptors ALK4/ACVR1B and ALK5/TGFBR1 with IC50 values of 2.2×10$^{-7}$ for each. The profile of AZD-0530 was similar in its selectivity for BMP vs. Activin/TGF-$\beta$ type I receptors as previously observed for LDN-193189 (Mohedas A H et al, ACS Chemical Biology 2013), albeit with slightly less potency for ALK2/ALK1/ALK3 than observed for LDN-193189 or LDN-212854. Since the latter two compounds have been shown previously to be effective in animal models of fibrodysplasia ossificans progressiva (FOP), the activity of AZD-0530 was tested in two distinct mouse models of FOP.

AZD-0530 Prevents Heterotopic Bone Formation in the ACVR1$^{Q207D}$-Tg Mouse Model of Heterotopic Ossification To evaluate the therapeutic potential of AZD-0530 in treatment of FOP, the inventors first employed one of the currently available models of heterotopic ossification, Cre-inducible transgenic mouse which conditionally expresses the constitutively active ACVR1$^{Q207D}$ mutation (CAG-Z-eGFP-caALK2-Tg) as described in methods.

Figure 3A:
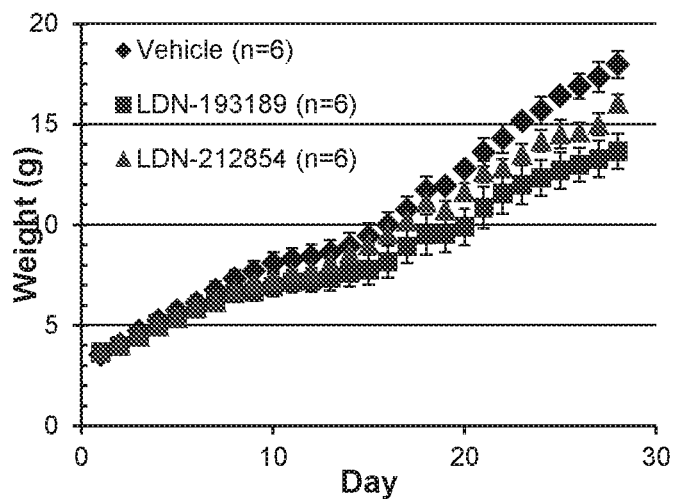
FIGS. 3A-3B. In vivo efficacy and tolerability of LDN-193189 and LDN-212854 in a mouse model of fibrodysplasia ossificans progressiva (FOP). Mice expressing an inducible constitutively-active ACVR1$^{Q207D}$ (CAG-Z-EGFP-caALK2) transgene were treated with vehicle, or pyrazolopyrimidine derivatives LDN-193189 or LDN-212854 (6 mg/kg intraperitoneally twice daily). Heterotopic ossification (not shown) and resulting loss of range-of-motion (FIG. 3B) were assessed following injection of Ad.Cre). Passive range-of-motion was progressively impaired in vehicle-treated mice starting on day 10, whereas mobility was almost entirely preserved in mice treated with LDN-193189 and LDN-212854. In contrast to treatment with AZD-0530, treatment with LDN-193189 or LDN-212854 was associated with weight loss of between 10%-25% relative to weights of vehicle-treated controls (FIG. 3A).
Figure 3B:
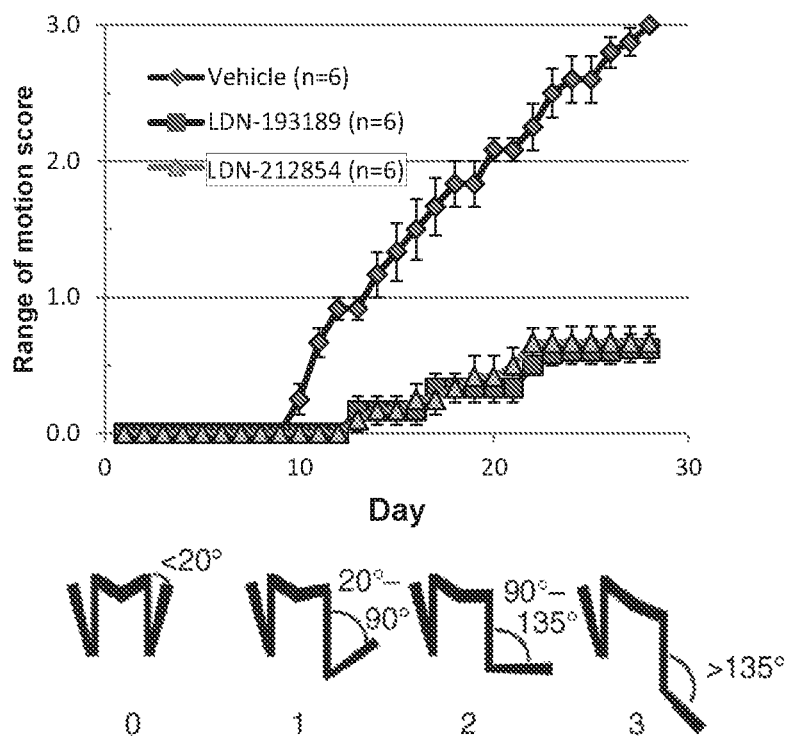

In CAG-Z-eGFP-caALK2-Tg animals, activation of the ACVR1$^{Q207D}$ transgene and associated GFP reporter is mediated by a single intramuscular injection of Adenovirus expressing Cre recombinase (Ad.Cre) in the left hindlimb on day 7 (P7). Injection with Ad.Cre activates the expression of a constitutively-active ACVR1$^{Q207D}$ transgene, as well as muscle necrosis and inflammation, which together result in the formation of heterotopic bone lesions within 7-10 days following Ad.Cre injection (Yu P B et al., Nat Med 2008). This model is thought to recapitulate aspects of clinical heterotopic ossification and FOP in which muscle injury and inflammation is seen to potentiate the formation of heterotopic bone in soft tissues. Untreated, this process normally leads to progressive loss of passive and active range-of-motion of the hip, knee and ankle joints that would progress over the following 3-4 weeks, accompanied by the formation of intramuscular heterotopic bone lesions visible by x-ray (FIG. 2). Mice treated with AZD-0530 by oral gavage (25 mg/kg once daily for 28 days) demonstrated significantly improved range of motion, and marked reduced heterotopic bone formation at the site of Ad.Cre injection by x-ray. GFP expression in the left hind limb confirmed efficient recombination of the ACVR1$^{Q207D}$ transgene at the injection site in all drug- and vehicle-treated animals. For comparison, administration of previously described BMP inhibitor compounds LDN-193189 and LDN-212854 (6 mg/kg i.p. twice daily) was also found to be effective in preserving range of motion and preventing heterotopic bone lesions on x-ray (Mohedas A H et al., ACS Chem Biol 2013), as shown in FIG. 3.

It was observed that treatment with LDN-193189 or LDN-212854 led to a relative 10-25% weight loss as compared to vehicle-treated animals under these regimens. In contrast, despite exhibiting strong efficacy at a daily dose of 25 mg/kg, AZD-0530 did not exert significant impact on the normal growth of the pups based on weight gain curves, indicating that AZD-0530 can be tolerated well in vivo at doses effective for inhibiting ALK2/ACVR1. Similarly, clinical phase I trials examining the effect of AZD-0530 at doses from 60 mg to 250 mg p.o. per day in healthy human adults for the modulation of osteoclast formation and bone turnover as potential therapy for osteoporosis and osteopenia demonstrated good tolerability (Hannon R A et al., J Bone Miner Res 2010). The inventors predict that over a similar span of doses, and most certainly at the very well tolerated range of doses up to 125 mg/kg in human adults, a dose at which bone turnover biomarkers are efficiently modulated by AZD-0530, similarly excellent efficacy on heterotopic bone formation in HO and FOP disease will be observed, while maintaining the excellent tolerability seen previously in other human trials.

Figure 4:
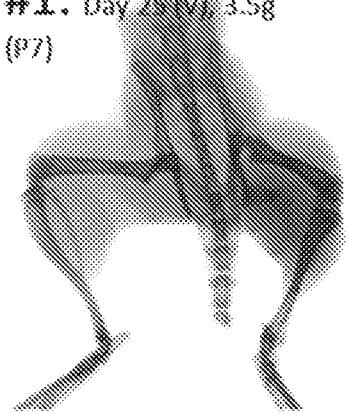
FIG. 4. Lack of in vivo efficacy of ZD-6474 in a mouse model of fibrodysplasia ossificans progressiva (FOP). Mice expressing an inducible constitutively-active ACVR1$^{Q207D}$ (CAG-Z-EGFP-caALK2) transgene were treated with vehicle, or ZD-6474 (25 mg/kg intraperitoneally twice daily). Heterotopic ossification was assessed radiographically following injection of Ad.Cre. All animals treated with vehicle developed progressive heterotopic ossification following challenge with Ad.Cre, as in previous studies. There was no evidence of improvement in radiographic HO or range-of motion in mice treated with ZD-6474 as compared to those treated with vehicle (n=3 each group), despite prior biochemical evidence that ZD-6474 inhibits ALK2 activity in vitro.
Figure 4:
Figure 4:
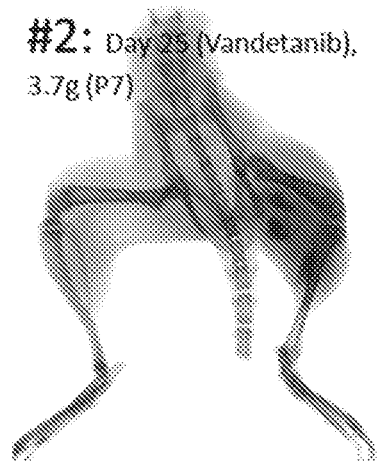
Figure 4:
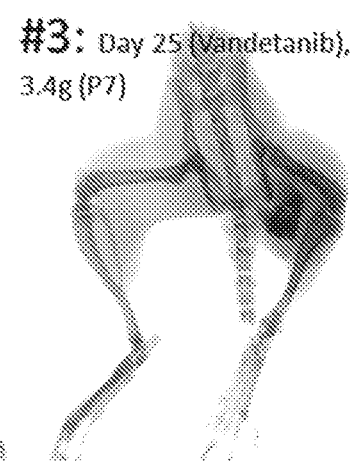
Figure 5A:
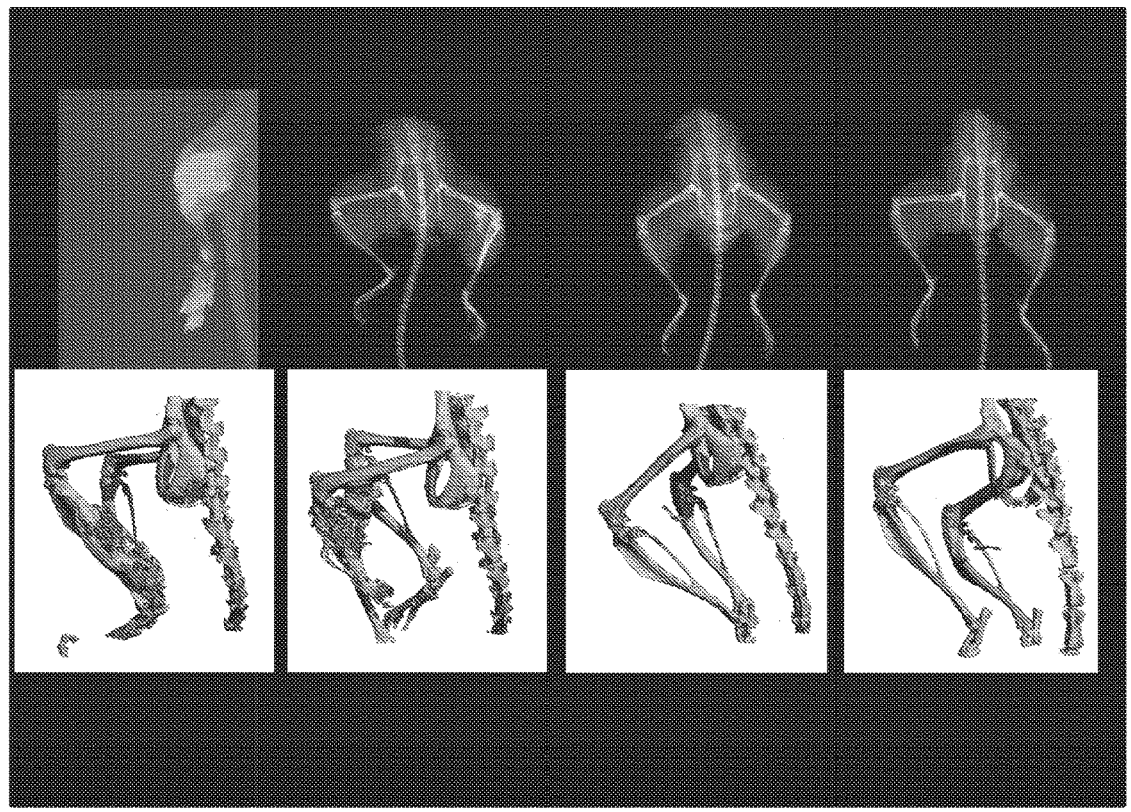
FIGS. 5A-5C. Early intervention with AZD-0530 following tissue injury and inflammation abrogates subsequent development of heterotopic ossification in a knock-in mouse model of FOP. ACVR1$^{[R206H]FlEx/+}$ knock-in mice, which conditionally express the ALK2$^{R206H}$ mutant receptor protein following Cre-mediated recombination (FIG. 5A), were challenged with Ad.Cre (1×10$^8$ pfu intramuscularly) on P7 and treated daily with 25 mg/kg of AZD-0530 or vehicle by oral gavage for 28 days. With or without drug treatment, no significant heterotopic ossification based on x-ray (FIG. 5A, lower panel), or range-of-motion loss (FIG. 5C) was observed for the first 28 days, at which time treatment with drug or vehicle was discontinued. However, following 40 days after Ad.Cre injection, slowly progressive loss of range-of-motion was observed and continued for at least 90 days of observation (FIG. 5C). Following treatment with AZD-0530 only for the first 28 days, drug-treated mice were protected from the progressive loss of range of motion or radiographic bone formation for the duration of the study up to 90 days (n=3 each group). No statistically significant change in weight was observed with AZD0530 treatment as compared to vehicle treated controls (FIG. 5B).
Figure 5B:
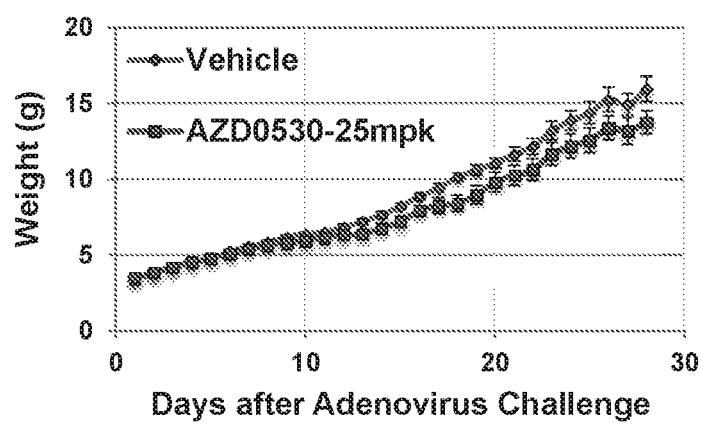
Figure 5C:
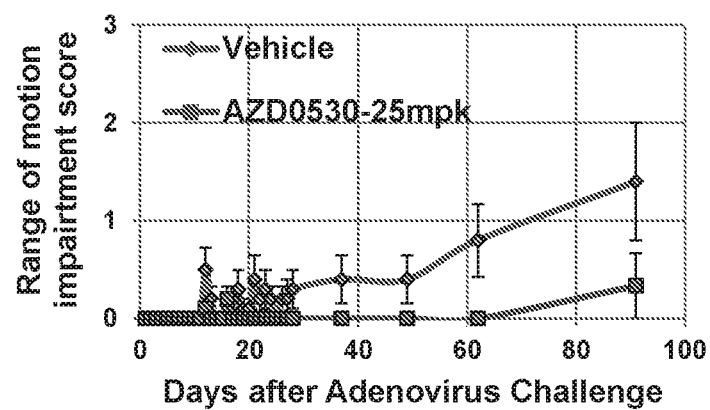
Figure 5C:
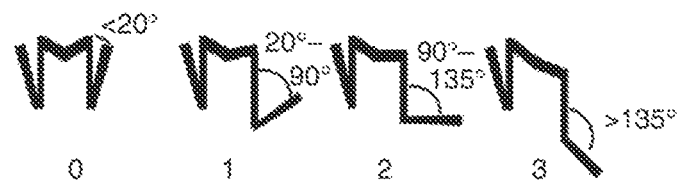

Not all Nanomolar Potency Inhibitors of ALK2/ACVR1 are Effective in Blocking Heterotopic Ossification in Models of Fibrodysplasia Ossificans Progressive Importantly, not all compounds with demonstrated biochemical affinity for or biochemical inhibition of ALK2/ACVR1 will exhibit efficacy in the inducible ACVR1$^{Q207D}$-Tg mouse model. Despite its demonstrated ability to bind and inhibit ALK2/ACVR1 with low nanomolar potency, ZD-6474, when administered at 25 mg/kg i.p. twice daily for 28 days to inducible ACVR1$^{Q207D}$-Tg mice following injection with Ad.Cre, did not significantly attenuate subsequent heterotopic ossification (FIG. 4), despite an exposure higher than previously shown to demonstrate in vivo efficacy against other target kinases in rodent models (Gule M K et al., Clin Cancer Res 2011).

AZD-0530 Prevents Heterotopic Bone Formation in the ACVR1$^{[R206H]FlEx/+}$ Mouse Model of Heterotopic Ossification The inventors next tested the efficacy of AZD-0530 in another model of FOP based on a knock-in mouse which conditionally expresses the ACVR1$^{R206H}$ mutation (ACVR1$^{[206H]FlEx/+}$) following Cre-loxP mediated recombination. Following Cre-mediated recombination, these mice express the highly conserved FOP-causing ACVR1$^{R206H}$ mutant allele, which has been found >97% of human cases of classic FOP (Kaplan F S et al., Hum Mut 2009). The human ACVR1$^{R206H}$ allele exhibits enhanced sensitivity for a variety of BMP and Activin ligands (Hatsell S et al, Sci Transl Med 2015) and has less intense biochemical activity than the constitutively-active ACVR1$^{Q207D}$ allele, and may thus represent a more faithful model of FOP disease in man. ACVR1$^{[R206H]FlEx/+}$ knock-in mice were challenged with Ad.Cre (1×10$^8$ pfu intramuscularly) on P7 and treated daily with 25 mg/kg of AZD-0530 or vehicle by oral gavage for 28 days. With or without drug treatment, no significant heterotopic ossification based on x-ray, or range-of-motion loss was observed for the first 28 days, at which time treatment with drug or vehicle was discontinued. However, following 40 days after Ad.Cre injection, slowly progressive loss of range-of-motion was observed and continued for at least 90 days of observation. Remarkably, despite treatment with AZD-0530 only for the first 28 days, prior to the development of any radiographic or clinical evidence of HO, drug-treated mice were protected from the progressive loss of range of motion or radiographic bone formation for the duration of the study up to 90 days (FIG. 5, n=3 each group). These results further confirm the in vivo efficacy of AZD-0530 in attenuating the FOP-promoting effects of an activating ALK2/ACVR1 mutation responsible for vast majority of cases of FOP disease in man. Moreover, these results demonstrate that when FOP is modeled in an authentic and physiologic manner by a combination of injury and expression of the human mutant allele under endogenous promoter control, suppression of the activity of ALK2/ACVR1 for a limited period of time following injury is sufficient to suppress the normal long term sequalae of tissue injury in individuals who are susceptible to HO, such as those who carry heterozygous activating mutations of ACVR1 such as in classic FOP.

It is likely that a short-term period of ALK2 and/or ALK3 pharmacologic suppression via compounds like AZD-0530 would be sufficient to prevent the development of HO in individuals with FOP, burn- or trauma-induced HO, or even inflammatory etiologies of HO, if the period of tissue inflammation, tissue damage and/or tissue repair were limited and might also define a period of susceptibility to either enhanced BMP signaling or enhanced ALK2 and/or ALK3 activity.

Methods

Cell-Based Assays of BMP/TGF-β Receptor Signaling Inhibition

C2C12 myofibroblast cells stably expressing firefly luciferase under the control of BMP-responsive promoter element (BRE-Luc) were generously provided by Dr. Peter ten Dijke (Leiden University Medical Center, NL). Human embryonic kidney 293T cells stably transfected with the TGF-β-responsive element fused to luciferase gene (CAGA-Luc) were a kind gift of Dr. Howard Weiner (Brigham and Women's Hospital, Boston, Mass.). C2C12 Bre-Luc and 293T CAGA-Luc cells were seeded at 20,000 cells in DMEM supplemented with 2% FBS per well in tissue culture treated 96-well plates (Costar® 3610; Corning). The cells were incubated for 1 h (37° C. and 10% $CO_2$) and allowed to settle and attach. AZD-0530 was diluted in DMSO, and diluted drug or DMSO vehicle only added to cells at final compound concentrations of 1 nM to 10 μM and a final concentration of DMSO of 2%. Cells were then incubated for 30 min. Adenovirus expressing constitutively active BMP and TGF-β type I receptors (Ad.caALK1-5), generously provided by Dr. Akiko Hata (University of California at San Francisco), were added to achieve a multiplicity of infection (MOI) of 100. Plates were incubated overnight at 37° C. Cell viability was assayed with an MTT (3-(4,5-dimethylthiazol-2-yl)-2,5-diphenyl tetrazolium bromide) colorimetric assay (Promega™) per manufacturer's instructions. Media was discarded and firefly luciferase activity was measured (Promega™) according to manufacturer's protocol. Light output was measured using a Spectramax™ L luminometer (Molecular Devices™) with an integration time of one second per well. Data was normalized to 100% of incremental BRE-Luc activity due to adenoviruses specifying caALK1, 2, or 3, or the incremental CAGA-Luc activity due to adenoviruses specifying caALK4 or 5, and also normalized to total cell counts based on MTT cell viability assay. Graphing and regression analysis by sigmoidal dose-response with variable Hill coefficient was performed using GraphPad™ Prism software.

ACVR1$^{Q207D}$-Tg and ACVR1$^{[R206H]FlEx/+}$ Mouse Models of Heterotopic Ossification Mice were maintained in accordance with Institutional Animal Care and Use Committee guidelines under approved experimental protocols. Cre-inducible ACVR1$^{Q207D}$ (CAG-Z-eGFP-caACVR1-Tg) transgenic mice were a generous gift from Dr. Yuji Michina (University of Michigan, Ann Harbor, Mich.) as previously described (Fukuda T et al., Genesis 2006). ACVR1$^{[R206H]FlEx/+}$ mice were kindly provided by Aris Economides (Regeneron Pharmaceutical, Inc.) as previously described (Hatsell S et al., Sci Transl Med 2015). Heterotopic bone formation in these mice was introduced via single retro-popliteal injection of adenoviral Cre-recombinase at 1×10$^8$ PFU at postnatal day 7 (P7). Mice (n=3-8 per group) were treated once a day for 4 weeks with AZD-0530 at 25 mg kg$^{-1}$ by oral gavage dissolved in a vehicle consisting of 5% DMSO and 95% peanut oil, or vehicle alone. Bone formation as a function of a loss of passive range of motion, via dorsiflexion of the left ankle joint was assessed daily. A score was assigned based on dorsiflexion angle (0=normal flexion, <30°, 1=mildly impaired, ≥30° and <90°, 2=moderately impaired, ≥90° and <135°, and 3=severely impaired, ≥135°). On day 35 for inducible ACVR1$^{Q207D}$ mice, and on day 90-120 for inducible ACVR1$^{R206H}$ a mice were sacrificed and imaged via X-ray radiography (MS FX In-Vivo Pro: Carestream Health). Micro-computed tomography (micro-CT) imaging was carried out on samples fixed overnight in 1% paraformaldehyde followed by scanning (µCT35, ScanCo).

Summary

AZD-0530/Saracatinib initially developed as a Src/Abl inhibitor for cancer.

Other targets identified such as ACVR1.

Comparison of the binding mode with DM and LDN shows it makes very similar contacts and occupies the pocket in a similar fashion.

AZD-0530 is a potent inhibitor of ACVR1 and is ×30 selective against TGFBR1

Given its potency and clinical safety it has applications to rare diseases such as FOP which were not linked to the initially designed target (Src/abl).

This is particularly important given the severity and rarity of FOP where rapid development of treatments is desirable but efforts are hampered by the small patient group.

Saracatinib (AZD-0530) was initially developed as a potent, orally available inhibitor of v-src sarcoma (Schmidt-Ruppin A-2) oncogene homolog.

The invention claimed is:

1. A method for treating abnormal bone in a soft tissue or preventing additional abnormal bone formation in a soft tissue of a subject, the method comprising: administering a therapeutically effective amount of a pharmaceutical composition comprising AZD0530 or AZD0424 to a subject having abnormal bone formation in a soft tissue, thereby treating or preventing additional formation of abnormal bone in a soft tissue of the subject.

2. The method of claim 1, further comprising a step of detecting the presence of abnormal bone formation in the subject prior to treatment.

3. The method of claim 1, wherein the subject has been subjected to a musculoskeletal trauma, a spinal cord injury or a central nervous system injury.

4. The method of claim 1, wherein the formation of abnormal bone is associated with a heterotopic ossification disease.

5. The method of claim 4, wherein the heterotopic ossification disease is selected from the group consisting of: acquired heterotopic ossification, fibrodysplasia ossificans progressive, anklyosing spondylosis, traumatic heterotopic ossification, burn- or blast-injury associated heterotopic ossification, and joint replacement surgery associated heterotopic ossification.

6. The method of claim 1, wherein the therapeutically effective amount of AZD0530 comprises a dose within the range of 5 mg/kg to 250 mg/kg.

7. The method of claim 1, wherein the therapeutically effective amount of AZD0530 does not cause weight loss greater than 20% of total body mass.

8. The method of claim 1, wherein the soft tissue comprises muscles, tendons, ligaments and/or fascia.

9. The method of claim 1, wherein at least one additional agent is administered to the subject.

10. The method of claim 9, wherein the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-1 signaling.

* * * * *

UNITED STATES PATENT AND TRADEMARK OFFICE
CERTIFICATE OF CORRECTION

| | |
|---|---|
| PATENT NO. | : 10,369,152 B2 |
| APPLICATION NO. | : 15/550139 |
| DATED | : August 6, 2019 |
| INVENTOR(S) | : Yu et al. |

It is certified that error appears in the above-identified patent and that said Letters Patent is hereby corrected as shown below:

In the Specification

At Column 1, Line 16:
Insert the following heading and paragraph:
--GOVERNMENT SUPPORT
This invention was made with government support under AR057374 awarded by the National Institutes of Health. The government has certain rights in the invention.--

Signed and Sealed this
Second Day of May, 2023

Katherine Kelly Vidal
*Director of the United States Patent and Trademark Office*